United States Patent [19]

Keen

[11] Patent Number: 5,020,536

[45] Date of Patent: Jun. 4, 1991

[54] POSTOPERATIVE CRYOKINETIC THERAPY APPARATUS AND METHOD

[76] Inventor: Robert E. Keen, 507 South Second Street, Champaign, Ill. 61820

[21] Appl. No.: 832,695

[22] Filed: Feb. 25, 1986

[51] Int. Cl.$^5$ .............................................. A61F 7/00
[52] U.S. Cl. .................................... 128/402; 128/163
[58] Field of Search ................. 2/171.2; 128/163, 164, 128/380, 400, 402, 76 R B

[56] References Cited

U.S. PATENT DOCUMENTS

| | | | |
|---|---|---|---|
| 1,110,772 | 9/1914 | Gunderman | 128/164 |
| 1,872,642 | 8/1932 | Welsh | 128/163 |
| 3,491,761 | 1/1970 | Baker | 128/402 |
| 3,759,256 | 9/1973 | O'Malley | 128/164 X |
| 4,055,188 | 10/1977 | Pelton | 128/402 |
| 4,190,054 | 2/1980 | Brennan | 128/402 |

*Primary Examiner*—Mickey Yu
*Attorney, Agent, or Firm*—Rogers & Killeen

[57] ABSTRACT

A postoperative cryokinetic therapy apparatus for selectively positioning a cold pack such as ice on the face of a patient following oral and maxillofacial surgery and for retaining the cold pack in the selected position during the patient's exercise of the jaw muscles. The apparatus comprises two vertical and one horizontal strap selectively adjustable and secured by velcro to facilitate the positioning of the cold pack. The vertical strap contains pouches on the patients facing side thereof for removably receiving sealable containers for ice or the like.

8 Claims, 1 Drawing Sheet

POSTOPERATIVE CRYOKINETIC THERAPY APPARATUS AND METHOD

BACKGROUND OF THE INVENTION

The present invention relates to postoperative cryokinetic therapy apparatus and more particularly to the apparatus by which a cold applicator may be selectively applied to a preselected position on the face of a patient following oral and maxillofacial surgery and retained in that position during the patient's exercise of the jaw muscles.

The beneficial effects of cold therapy are well known and cold therapy has been applied to the head. Such cold applicators generally take the form of an ice bag placed atop the head and secured around the head as in the Rioux U.S. Pat. No. 1,870,143 dated Aug. 2, 1932, secured by a string or the like beneath the chin as shown in the Finkelstein U.S. Pat. No. 1,127,221 dated Feb. 2, 1915, or by a combination of a single vertical and horizontal strap as in the Rioux, et al. U.S. Pat. No. 1,511,175 dated Oct. 14, 1924.

It is also known to apply cold to the forehead by a horizontal strap as shown in the Augustine U.S. Pat. No. 1,345,906 dated July 6, 1920, or to the neck area by means of collars, e.g., held in place by a single head strap as in the Glennan U.S. Pat. No. 1,910,328, dated May 23, 1933 or by two vertical straps as in the Reach U.S. Pat. No. 2,071,706 dated Feb. 23, 1937.

It is more difficult to apply cold to the side of a patient's head, and the known apparatus therefor have included an ice bag configured to fit around the ear to the rear thereof with a single under-the-chin strap such as shown in the Meinecke U.S. Pat. No. 919,614 dated Apr. 27, 1909. Attempts to make such bags adjustable, and to apply the cold therapy to the areas of the jaw forward of the ear include a vertically adjustable harness over the top of the patient's head and under the patient's chin, the straps having multiple openings along the length thereof to retain an ice bag in a selected location as shown in the Baker U.S. Pat. No. 3,491,761 dated Jan. 27, 1970.

More recent attempts to selectively position a cold pack on the face of a patient have included elastic bandages covering a substantial part of the patient's head and secured both around the patient's neck and over the patient's head. Velcro straps are positioned on the outside surface of the elastic bandage so that a cold pack may be selectively secured to the bandage on the outside thereof as shown in the Brennan U.S. Pat. No. 4,190,054 dated Feb. 26, 1980.

None of the generally known apparatus provide the adjustability desired for postoperative cryokinetic therapy and generally do not provide for the location of the cold pack on side of the apparatus facing the patient. Moreover, movement of the patient's jaw is often unacceptably restricted and/or the device is uncomfortable, particularly during periods of long wear and jaw exercise.

It is accordingly an object of the present invention to obviate these and other problems associated with known devices and to provide a postoperative cryokinetic therapy device which is comfortable to wear, selectively and easily positionable with the capability of long wear without discomfort, with removable cold packs.

These and many other objects and advantages will be readily apparent to one skilled in the art from the claims when read in connection with the following detailed description and accompanying drawings.

THE DRAWINGS

THE DETAILED DESCRIPTION

Figure 1:
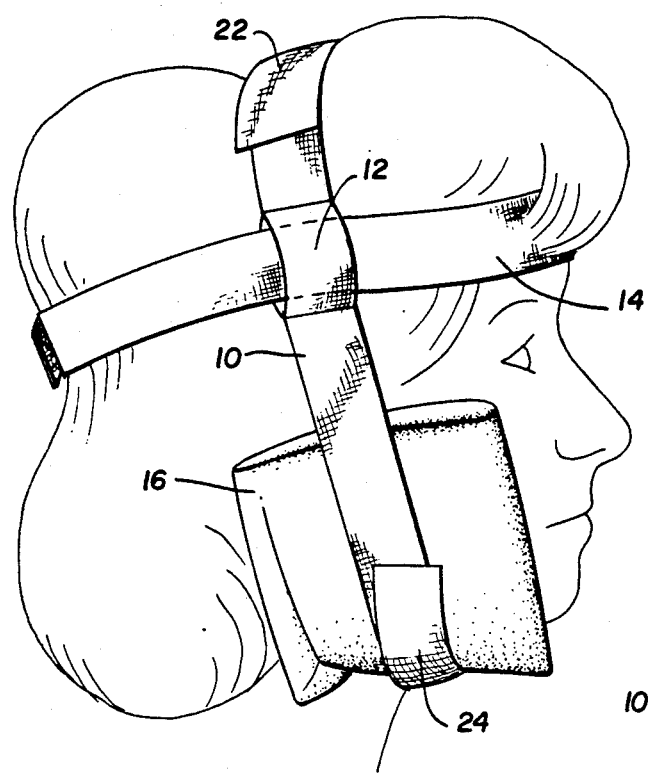
FIG. 1 is a pictorial view of the postoperative cryokinetic therapy device of the present invention when placed on the head of a patient.
Figure 2:
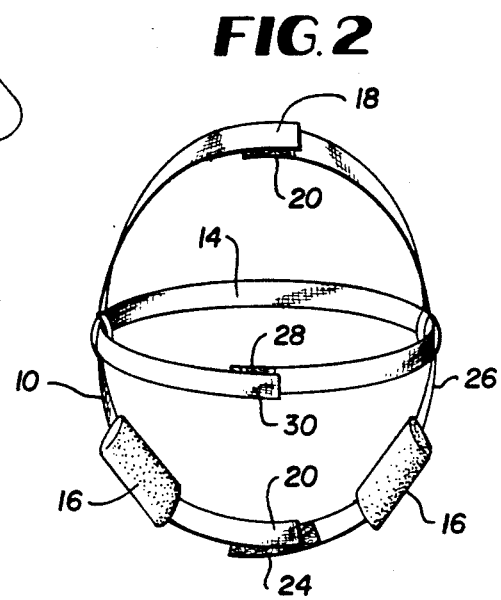
FIG. 2 is a pictorial view of the device of FIG. 1 from the front.
Figure 3:
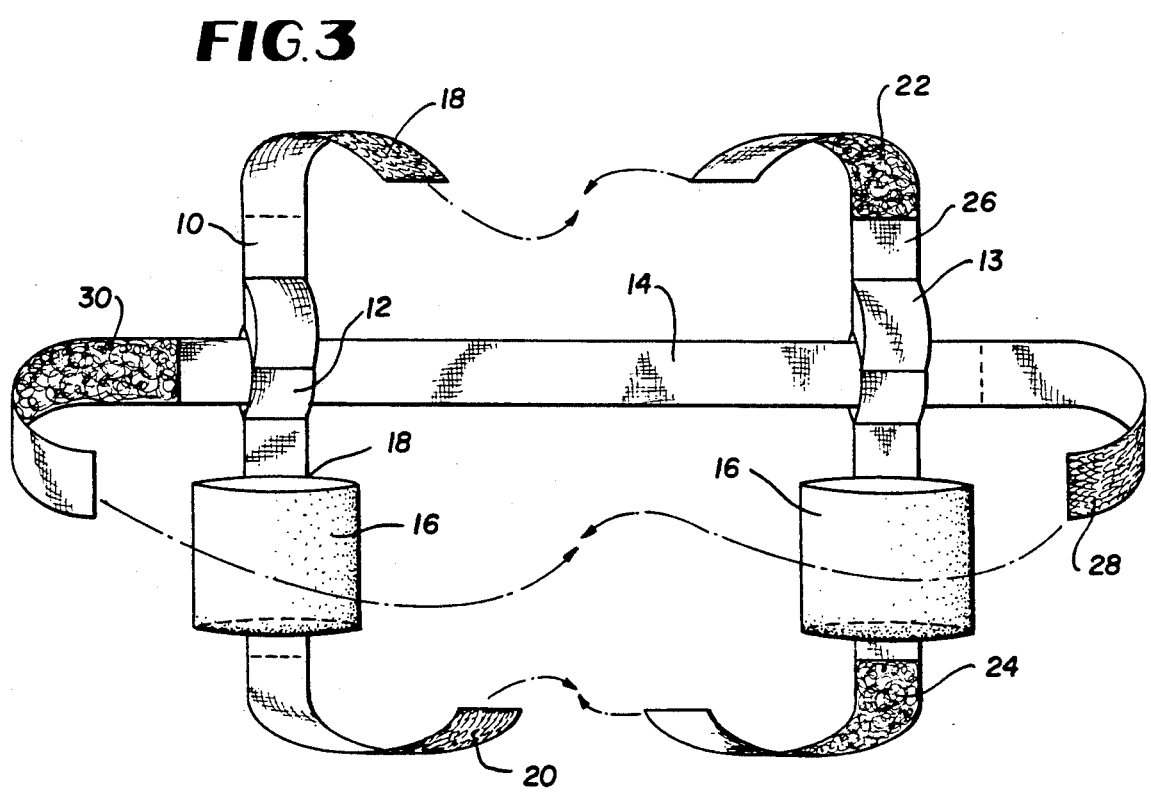
FIG. 3 is a pictorial view of the postoperative cryokinetic therapy device of FIG. 1 showing the construction thereof.

With reference to the figures, the device of the present invention in a preferred embodiment includes a first vertical strap 10 which is made of any suitable conventional material to form a strap of approximately 1 inch in width and approximately 18 inches in length. At the approximate center of the strap 10 is a loop 12 formed in any suitable conventional manner to receive the flat horizontal strap 14. The loop 12 may be formed by the stitching or otherwise securing of a small piece of strap material to the strap, or by the creation of the vertical strap 10 from two pieces of strap material overlapped and stitched at spaced apart intervals to form the loop therebetween. More than one loop may be provided e.g., a loop 13 to increase the range of adjustment of the distance between the pouch 16 for the cold pack and the horizontal strap 14.

With continued reference to the figures, the pouch 16 is secured to the vertical strap 10 on the patient facing side thereof, desirably only at the top thereof by a single line of stitching 18. The pouch 16 may be made of any suitable conventional material such as nylon or other synthetic woven fabric.

The vertical strap 10 may be provided with a velcro fastner for removable attachment of the mating velcro surfaces of 22, 24, of the second vertical strap 26. While the hook portions 18, 20 of the velcro do not have to be on the same vertical strap, it is important for the comfort of the patient that the hook surfaces be on the flat surface of the strap facing away from the patient, and that the eye portions 22, 24 be on the flat surface facing the patient. Similarly, the horizontal strap 14 may be provided with a hook velcro surface 28 and then inwardly facing eye velcro surface on the inwardly facing 30 thereof.

It is desirable for the adjustability of the apparatus that the velcro surfaces aggregate approximately 50% of the length of the vertical straps 10, 26, i.e., approximately 4.5 inches each or for a total of 9 inches. The velcro surfaces of the horizontal strap 14 are of approximately the same length for the same reason. The vertical straps 10, 26 are desirably of the same length with the horizontal strap approximately 150% of the length of the vertical straps 10, 26.

In use, the cold pack may be any suitable conventional sealable container. Small resealable bags of crushed ice have been found suitable for this purpose. The cold packs may be of any desired shape and size appropriate for selective insertion into the pouches 16. The cold packs may be placed only on one vertical side of the vertical strap, or both, or in horizontal layer across either the bottom portion or the entirety of the pouch 16.

In use, the ice pack of the desired size is positioned within the pouch 16 and the pouch positioned against the patient's face. The vertical straps 10, 26 are thereafter adjusted to comfortably retain the ice pack in the predetermined position. The ice packs may be replaced without disturbing the adjustment of the vertical and horizontal straps. With the vertical straps adjusted to the comfort of the patient, the horizontal strap may be threaded through a selected loop and the ends 28, 30 fastened.

Once the apparatus has been positioned on the head of the patient, the patient may with comfort, exercise the jaw muscles by chewing or the like and thereby achieve the desirable medical benefits from cryokinetic therapy.

While the present invention has been described with respect to a preferred embodiment, it will be readily apparent to those skilled in the art that various modifications and improvements may be made without departing from the scope and spirit of the invention. Accordingly, it is to be understood that the invention is not to be limited by the specific disclosed embodiments, but by the scope of the appended claims when accorded a full range of equivalents.

What is claimed is:

1. Apparatus for postoperative cryokinetic therapy following oral and maxillofacial surgery comprising:
    a first flat vertical strap of predetermined length having a loop intermediate the ends thereof;
    a first pouch carried by said first vertical strap on the flat side thereof facing the patient;
    first and second "VELCRO"-like hook surfaces carried respectively by said first strap over adjacent opposite ends of said first strap on the flat side thereof facing away from the patient, said "VELCRO"-like surfaces aggregating in length approximately fifty percent of the length of said first strap;
    a second flat vertical strap having a length approximating that of said first strap and a loop intermediate the ends thereof;
    first and second "VELCRO"-like eye surfaces carried respectively by said second strap adjacent opposite ends of said second strap on the flat side thereof facing the patient, said "VELCRO"-like surface aggregating in length approximately fifty percent of the length of said second strap;
    a flat horizontal strap passing through the loops in said first and second vertical straps, said horizontal strap having a length approximately 150 percent of the length of said first and second straps and having a "VELCRO"-like hook surface adjacent one end thereof on the flat side facing away from the patient and a "VELCRO"-like eye surface adjacent the other end thereof on the flat side thereof facing the patient, said patient, said "VELCRO"-like surfaces aggregating in length approximately thirty-five percent of the length thereof; and
    a sealable container for ice sized and configured for removable insertion into said first pouch to thereby apply cold to a preselected area of the patient's face during the exercise of the jaw muscle by the patient.

2. The postoperative cryokinetic therapy apparatus of claim 1 including a second pouch carried by said second vertical strap intermediate the ends thereof.

3. The postoperative cryokinetic therapy apparatus of claim 2 wherein said loops are nearer to the upper end of the strap when worn by the patient than to the lower end; and
    wherein said first pouch is attached to said first vertical strap approximately halfway between said loop and the velcro-like surface carried by the lower end thereof.

4. The postoperative cryokinetic therapy apparatus of claim 1 wherein said first pouch is non-removably secured to said first strap at only one place along the length thereof.

5. Apparatus for postoperative cryokinetic therapy following oral and maxillofacial surgery comprising:
    a first flat vertical strap of predetermined length having a first loop and a second loop intermediate the ends thereof;
    a first pouch carried by said first vertical strap on the flat side thereof facing the patient;
    first and second "VELCRO"-like hook surfaces carried respectively by said first strap over adjacent opposite ends of said first strap on the flat side thereof facing away from the patient, said "VELCRO"-like surfaces aggregating in length approximately fifty percent of the length of said first strap;
    a second flat vertical strap having a length appropriating that of said first strap and a first loop and a second loop intermediate the ends thereof;
    first and second "VELCRO"-like eye surfaces carried respectively by said second strap adjacent opposite ends of said second strap on the flat side thereof facing the patient, said "VELCRO"-like surface aggregating in length approximately fifty percent of the length of said second strap;
    a flat horizontal strap passing through one of the loops in each of said first and second vertical straps, said horizontal strap having a length of said first and second straps and having a "VELCRO"-like eye surface adjacent one end thereof on the flat side facing away from the patient and a "VELCRO"- like eye surface adjacent the other end there of on the flat side thereof facing the patient, said "VELCRO"-like surfaces aggregating in length approximately thirty-five percent of the length thereof; and
    a sealable container for ice sized and configured for removable insertion into said first pouch to thereby apply cold to a preselected area of the patient's face during the exercise of the jaw muscle by the patient.

6. Cryokinetic therapy apparatus comprising:
    first and second vertical straps;
    a pouch carried by said first vertical strap on the patient facing side thereof;
    means for removably attaching the respective ends of said vertical straps to thereby vertically adjust the position of said pouch with respect to the face of the patient;
    a horizontal strap;
    means for connecting said horizontal strap to said vertical straps to thereby selectively position said pouch horizontally with respect to the face of the patient; and
    a cold pack adapted to be carried in said pouch whereby cold can be applied to the face of the patient during cryokinetic therapy.

7. A method of performing postoperative cryokinetic therapy following oral and maxillofacial surgery comprising the steps of:

a) providing a cold pack and a headstrap device for carrying the cold pack, the headstrap device comprising a horizontal strap, two vertical straps each having at least one loop intermediate the ends thereof for connection with the horizontal strap and a pouch for retaining the cold pack;

b) positioning the cold pack within the pouch;

c) positioning the pouch in a predetermined position against the patient's face;

d) adjusting the vertical straps to comfortably retain the ice pack in the predetermined position while at the same time allowing exercise of the jaw muscle;

e) threading the horizontal strap through the loops of the vertical straps;

f) fastening the horizontal strap to the head; and g) replacing the cold pack as necessary without removing the head strap device to allow continuing application of cold during therapy.

8. The method of claim 7 wherein each of the vertical straps has at least two loops intermediate the ends thereof to increase the range of adjustment of the distance between the pouch for the cold pack and the horizontal strap, and also comprising the step of selecting the desired loops through which to thread the horizontal strap to effect desired positioning of the strap and cold pack relative to the head and face.

* * * * *